(12) United States Patent
Bruno et al.

(10) Patent No.: US 10,292,765 B2
(45) Date of Patent: May 21, 2019

(54) DEPTH CONTROLLED PHOTOABLATION OF HUMAN OR ANIMAL TISSUE

(71) Applicant: Advanced Osteotomy Tools—AOT AG, Basel (CH)

(72) Inventors: Alfredo E. Bruno, Biel-Benken (CH); Philippe Cattin, Windisch (CH); Waldemar Deibel, Wrexen/Diemelstadt (DE)

(73) Assignee: Advanced Osteotomy Tools—AOT AG, Basel (CH)

( * ) Notice: Subject to any disclaimer, the term of this patent is extended or adjusted under 35 U.S.C. 154(b) by 702 days.

(21) Appl. No.: 14/758,064

(22) PCT Filed: Dec. 27, 2013

(86) PCT No.: PCT/EP2013/078090
§ 371 (c)(1),
(2) Date: Jun. 26, 2015

(87) PCT Pub. No.: WO2014/102355
PCT Pub. Date: Jul. 3, 2014

(65) Prior Publication Data
US 2015/0327930 A1 Nov. 19, 2015

(30) Foreign Application Priority Data
Dec. 28, 2012 (EP) .................. 12199762

(51) Int. Cl.
*A61B 18/20* (2006.01)
*A61B 5/00* (2006.01)
(Continued)

(52) U.S. Cl.
CPC .......... *A61B 18/20* (2013.01); *A61B 5/0066* (2013.01); *A61B 18/203* (2013.01); *A61B 34/30* (2016.02);
(Continued)

(58) Field of Classification Search
CPC ....... A61B 18/20; A61B 18/203; A61B 18/26; A61B 2017/00106; A61B 2018/00452;
(Continued)

(56) References Cited

U.S. PATENT DOCUMENTS 7,649,153 B2 * 1/2010 Haight .................. A61B 18/26
219/121.69
2008/0058782 A1 3/2008 Frangineas et al.
(Continued)

FOREIGN PATENT DOCUMENTS

EP 2119408 A1 11/2009
WO WO 2011/035792 A1 3/2011

OTHER PUBLICATIONS

Office Action issued in European Application No. 13 821 834.2-1666 dated May 16, 2017.

*Primary Examiner* — Elmer M Chao
(74) *Attorney, Agent, or Firm* — Hoffmann & Baron, LLP

(57) ABSTRACT

A photoablation device includes a laser source to propagate a focused laser beam with a beam waist, wherein a radius of the beam increases from the waist in a direction of propagation of the beam; an adjusting structure to adjust an intensity of the beam; a position detector to detect a position of the source in relation to the tissue; a positioning device to move the source in relation to the tissue; and a controller. The controller is to define a photoablation zone of the beam, wherein the zone ends in a cutting face located offset from the waist in the direction of propagation; adjust the intensity of the beam at the face of the zone using the adjusting structure; and move the beam towards the tissue by using the positioning device, wherein the position of the source detected by the position detector is evaluated.

19 Claims, 2 Drawing Sheets

(51) Int. Cl.
*A61B 18/00* (2006.01)
*A61B 17/00* (2006.01)
*A61B 90/00* (2016.01)
*A61B 34/20* (2016.01)
*A61B 34/30* (2016.01)

(52) U.S. Cl.
CPC ............. *A61B 2017/0019* (2013.01); *A61B 2017/00747* (2013.01); *A61B 2018/0072* (2013.01); *A61B 2018/0088* (2013.01); *A61B 2018/00565* (2013.01); *A61B 2018/00577* (2013.01); *A61B 2018/00601* (2013.01); *A61B 2018/00642* (2013.01); *A61B 2018/00648* (2013.01); *A61B 2018/00845* (2013.01); *A61B 2034/2063* (2016.02); *A61B 2090/049* (2016.02); *A61B 2090/3735* (2016.02)

(58) Field of Classification Search
CPC ........... A61B 2018/00636; A61B 2018/00642; A61B 2018/625; A61B 2034/2051; A61B 2034/2055; A61B 2034/2063; A61B 2034/2065
See application file for complete search history.

(56) References Cited

U.S. PATENT DOCUMENTS

2010/0119808 A1* 5/2010 Li ..................... B23K 26/0057
428/312.6
2015/0080748 A1* 3/2015 Hubbert ............... A61B 5/7282
600/481

* cited by examiner

DEPTH CONTROLLED PHOTOABLATION OF HUMAN OR ANIMAL TISSUE

CROSS-REFERENCE TO RELATED APPLICATIONS

This application is the U.S. National Phase of International Patent Application No. PCT/EP2013/078090, filed on 27 Dec. 2013, which claims benefit of European Patent Application No. 12199762.1, filed on 28 Dec. 2012, the contents of which are incorporated herein by reference in their entireties.

TECHNICAL FIELD

The present invention relates to a method in which a focused laser beam with a beam waist is provided to a human or animal tissue and, more particularly, to a device with which such a method can be implemented, and a computer program controlling such a device. Such methods, devices, and computer programs can be used for photoablating and thereby cutting human or animal tissue.

BACKGROUND ART

For cutting human or animal hard tissue, such as bone or nail tissue, various methods and devices are applied today. In recent years, photoablation using laser beams turned out to be a feasible alternative to known tools and methods. Particularly, in osteotomy, laser induced photoablation became of increasing interest as an alternative to known mechanical tools such as saws, chisels, or drills. The aim of such laser induced photoablation is to increase preciseness and operability while decreasing collateral damage, e.g., caused by direct contact of the mechanical tools with the bone.

For example, in WO 2011/035792 A1 a computer assisted and robot guided laser osteotome medical device is described. This medical device includes a laser head mounted to a robotic arm. The robotic arm has several degrees of freedom such that the laser head can be precisely adjusted in preferred positions and orientations. Like this, it is possible to precisely provide a laser beam onto bone tissue and to photoablate the bone such that it is cut along a predefined osteotomic line. For determining and adjusting the beam position in relation to the bone, the medical device has an autotracking system. Using the autotracking system, the position and orientation of the bone can be monitored and the laser head can be adjusted in order to prevent a deviation of the cutting from the predefined osteotomic line.

A common problem in known laser induced photoablation of human or animal hard tissue relates to controlling cutting depth and beam intensity. In contrast to laser induced photoablation widely used in micromachining of non-biological materials such as metals and plastics, issues with respect to collateral damage are of crucial importance when photoablating human or animal hard tissue. Such collateral damage, e.g., carbonization, can occur due to heating caused by inappropriate laser beam intensities in tissue neighboring the osteotomic or cutting line. Or, collateral damage can also occur due to photoablation beyond the depth of the targeted hard tissue. Making these problems even more difficult to handle, in contrast to the mentioned non-biological materials, human or animal hard tissues of the same type usually differ from one individual to the other. Furthermore, human or animal hard tissues usually are not homogeneous such that the photoablation properties of the tissue can vary within one single tissue target, particularly, depending on the cutting depth. For preventing such excess or unwanted photoablation, depth of the photoablation in the tissue is usually optically monitored, e.g., using optical coherence tomography (OCT). However, such monitoring is, on one hand, usually rather complicated and can, on the other hand, be impaired by other factors of the photoablation such as by debris, water, or blood.

Therefore, there is a need for a method and device allowing convenient improved photoablation of human or animal tissue using a laser beam particularly in terms of collateral damage caused to the tissue by the laser beam.

SUMMARY

According to the invention, the aforementioned need is settled by a method of depth controlled photoablation of human or animal tissue as it is defined by the features of independent claim 8, and by a photoablation device as it is defined by the features of independent claim 1. Preferred embodiments are subject of the dependent claims.

In particular, the gist of the invention is the following. A method of depth controlled photoablation of human or animal tissue includes the steps of: providing a focused laser beam with a beam waist, wherein a radius of the laser beam increases from the beam waist in a direction of propagation of the laser beam; defining a photoablation zone of the laser beam, wherein the photoablation zone ends in a cutting face which is located offset from the beam waist in the direction of propagation of the laser beam; adjusting the laser beam such that an intensity at the cutting face of the photoablation zone is too low to photoablate the tissue; moving the laser beam in relation to the tissue such that the cutting face of the photoablation zone is arranged at a surface of the tissue; continuously increasing intensity of the laser beam until the intensity at the cutting face of the photoablation zone is sufficiently high to photoablate the tissue; and moving the laser beam towards the tissue. Preferably, the method according to the invention is performed to the human or animal tissue in vitro.

In the context of the invention, human or animal tissue relates to any tissue suitable for being cut or drilled by laser induced photoablation. The tissue can be a hard tissue such as nail tissue, tooth tissue, or the like, and particularly bone tissue. The term "intensity" in connection with the laser beam relates to energy per time per area. In order to make photoablation of the tissue possible with the laser beam, the intensity of the laser beam has to be above a specific threshold. Beyond others, this threshold depends on the properties of the tissue. The term "continuously" with regard to the increasing of the laser beam intensity relates to fluent increasing, as well as to iterative or stepwise increasing. The term "photoablation" or laser ablation generally relates to a process of removing material from a solid or sometimes liquid surface by irradiating the material with a laser beam. With the photoablation according to the invention, slits, cuts, and/or holes can be provided in the tissue. The steps of adjusting the laser beam such that the intensity at the cutting face of the photoablation zone is too low to photoablate the tissue and continuously increasing the intensity of the laser beam until the intensity at the cutting face of the photoablation zone is sufficiently high to photoablate the tissue can be called calibration. The direction of propagation of the laser beam can also be referred to as a distal direction.

In some embodiments, and in the absence of supplementary optical elements, the laser beam increases over essentially its whole extent, i.e., it diverges. In such cases, the beam waist can be located at or near a laser source propagating the laser beam. However, typically for focused laser beams, the radius of the laser beam also increases from the beam waist against the direction of propagation of the laser beam such that the beam waist defines a narrowest section or focal point of the laser beam.

Within the method according to the invention, the depth of the photoablation into the tissue can conveniently be controlled and determined by the movement of the laser beam towards the tissue. In particular, the depth can correspond to the movement of the laser beam towards the tissue. Furthermore, the photoablation energy or intensity can precisely be adjusted in accordance with the properties of the tissue. Like this, it is possible to take account of the individual properties of the tissue and to minimize collateral damage and particularly heating of the tissue such that, e.g., carbonization of the tissue can be prevented.

Preferably, the photoablation zone of the laser beam corresponds to a Raleigh zone of the laser beam. Defining the photoablation zone to correspond to the Raleigh zone of the laser beam allows for implementing the photoablation zone in a well-established fashion and to precisely define the cutting face of the laser beam at the distal end of the Raleigh zone. Also, as the laser beam increasingly diverges outside the Raleigh zone, the intensity correspondingly decreases. Therefore, defining the cutting face to be at the distal end of the Raleigh zone allows for an efficient photoablation, e.g., in terms of energy consumption, in terms of delimitation of the cutting face, and in terms of cutting or drilling abilities.

Preferably, the intensity of the laser beam is adjusted by adjusting current and/or voltage provided to a laser source propagating the laser beam and/or by adjusting a length of a pulse of the laser beam. Such adjustment of the laser beam allows for a comparably simple, precise, and efficient implementation.

Preferably, it is continuously sensed if the tissue is photoablated and the increasing of the intensity of the laser beam is stopped when it is sensed that the photoablation of the tissue starts. Like this, the threshold of the intensity required for photoablating the tissue can be precisely and conveniently determined. By stopping the increasing of the intensity once the threshold is reached, the intensity can be exactly adjusted to the properties of the tissue and any unnecessary heating of the tissue can be prevented.

It is preferably acoustically sensed if the tissue is photoablated or not. Such acoustical sensing can, e.g., be performed by positioning a microphone, particularly, a laser microphone, and/or a piezoelectric pressure transducer, near or at the tissue. Like this, the threshold of the laser beam intensity necessary for photoablating the tissue can be precisely detected in a comparably simple manner.

Thereby, a frequency spectrum of an acoustically sensed wave is preferably monitored. The frequency spectrum depends on the acoustic impedance of the tissue. For example, applying laser beams with identical properties, comparably hard materials generate comparably high acoustic frequencies, whereas comparably soft materials generate comparably low acoustic frequencies. Thus, monitoring the acoustically sensed signal allows for recognizing changing properties of the tissue. Accordingly, suitable measures can be taken based on the monitored acoustic signal. For example, propagation of the laser beam can be stopped or recalibrated, as described in the following section, if it is detected that the tissue is getting softer such that the beam intensity should preferably be reduced.

Generally, optical coherence tomography (OCT) is an interferometric technique that is used as an optical signal acquisition and processing method. It captures micrometer-resolution, one-two and three-dimensional images from within optical scattering media such as biological tissue, e.g., the human or animal tissue. The use of relatively long wavelength light allows it to penetrate into the scattering medium. Depending on the properties of the light source superluminescent diodes, ultrashort pulsed lasers and supercontinuum lasers are employed. A relatively recent implementation of OCT, which is called frequency-domain OCT, provides advantages in signal-to-noise ratio, permitting faster signal acquisition. OCT systems are employed in diverse applications, including diagnostic medicine, ophthalmology, and cardiology to help diagnose coronary artery disease. OCT can also be used in conjunction with the present method to monitor the depth of the cut or drill by photoablation in real-time. As an alternative to the acoustic sensing described hereinbefore, or in addition to such acoustic sensing, it is preferably optically sensed if the tissue is photoablated by applying OCT. In particular, OCT can be used to anticipate outer bone-soft tissue interface or any intermediate position with high precision. Such sensing with OCT can allow for an efficient high precision control of the photoablation.

Preferably, the method further includes decreasing intensity of the laser beam such that the intensity at the cutting face of the photoablation zone is too low to photoablate the tissue again and continuously increasing intensity of the laser beam again until the intensity at the cutting face of the photoablation zone is sufficiently high to photoablate the tissue. Like this, the laser beam can be recalibrated during the photoablation process. This can be particularly helpful in cases where properties of the tissue are changing, e.g., with increasing depth of the photoablation. For example, human bone tissue usually is not fully homogenous and photoablation properties often change inwards in a bone. In particular, in consideration of the frequency spectrum acoustically sensed as described above, this allows for ongoing recalibration of the laser beam as soon as a change of tissue properties is detected by changing frequency spectrum.

Preferably, properties of the tissue are determined prior to continuously increasing the intensity of the laser beam, wherein the properties are considered when photoablating the tissue. In this context, properties can relate to dimensions, structure, and/or composition of the tissue. They can particularly include a thickness of the tissue. By considering the properties of the tissue, the photoablation process can be tailored and optimized to the given situation. Furthermore, these pre-determined properties can be combined with properties measured in an ongoing manner and determined such that the photoablation process can additionally be tailored and optimized to the given situation.

As mentioned hereinbefore, the human or animal tissue preferably but not necessarily is photoablated in vitro.

A further aspect of the invention relates to a photoablation device for photoablation of human or animal tissue. The photoablation device includes: a laser source being arranged to propagate a focused laser beam with a beam waist, wherein a radius of the laser beam increases from the beam waist into a direction of propagation of the laser beam, an adjusting structure being arranged for adjusting an intensity of the laser beam; a position detector for detecting a position of the laser source in relation to the tissue; a positioning device being arranged to move the laser source in relation to the tissue; and a controller unit being arranged to define a photoablation zone of the laser beam, wherein the photoablation zone ends in a cutting face which is located offset from the beam waist in the direction of propagation of the laser beam, to adjust an intensity at the cutting face of the photoablation zone of the laser beam by the adjusting structure, and to move the laser beam towards the tissue by the positioning device, wherein the position of the laser source detected by the position detector is evaluated.

In the context of the invention, the term "position" can relate to location and orientation of the laser source. The photoablation device allows for efficiently and conveniently implementing the method described above, thereby implementing the aspects and preferred effects as described in connection with the method.

The laser source can, e.g., be arranged to emit at wavelengths where water has strong absorption bands and can preferably include an Erbium solid state laser such as Er:YAG, Er/Pr:YAG, Ho:YAG or Er/Cr:YSGG, a holmium solid state laser such as Ho/Nd:YAG or Ho:YSGG, a diode laser, and/or a fiber laser. For example, the photoablation laser can have a pulse temporal width which is between 10 femtoseconds and 1 millisecond, preferably, between 10 nanoseconds and 800 microseconds. It can also be arranged to deliver a laser beam with an energy density between 1 millijoule per square centimeter and 100'000 joules per square centimeter, in particular, between 10 millijoules per square centimeter and 5 joules per square centimeter.

Preferably, the adjusting structure includes a current adjuster for adjusting current or voltage or both, current and voltage simultaneously, provided to the laser source propagating the laser beam, and/or a pulse adjuster for adjusting a length of a pulse of the laser beam. With such an adjusting structure, the photoablation device can be capable of efficiently and precisely adjusting intensity of the laser beam.

Preferably, the photoablation device further includes an acoustic sensor being arranged to sense an acoustic wave generated by the laser beam hitting the tissue and to provide a corresponding signal. Thereby, the controller unit preferably is arranged to evaluate the signal provided by the acoustic sensor in order to detect photoablation of the tissue. Like this, the threshold of the laser beam intensity necessary for photoablating the tissue can be precisely detected in a comparably simple manner. Thereby, the controller unit preferably is arranged to continuously increase intensity of the laser beam until photoablation of the tissue is detected, by evaluating the signal provided by the acoustic sensor. Such controller unit allows for precisely and conveniently adjusting the laser beam appropriately.

Preferably, the controller unit is arranged to monitor a frequency spectrum of the acoustic wave by evaluating the signal provided by the acoustic sensor. As described in greater detail above, in connection with the method according to the invention, such monitoring allows for recognizing changing properties of the tissue. Accordingly, suitable measures can be taken based on the monitored acoustic signal.

Preferably, the acoustic sensor is a microphone, and/or a piezoelectric pressure transducer, and/or a laser microphone. Such an acoustic sensor allows for a comparably simple implementation with appropriate precision and efficiency. As an alternative or in addition to the acoustic sensor, the photoablation device preferably further includes an optical coherence tomography structure with an optical sensor. Such OCT structure can be arranged to apply OCT as described above in connection with the method, wherein, in particular, the controller unit can be arranged to be involved in the OCT.

Another aspect of the invention relates to a computer program including program code being arranged to implement a controller unit of a photoablation device as described hereinbefore when being executed. Such a computer program allows for efficiently and conveniently implementing the method described above and controlling the device described above, thereby implementing the aspects and preferred effects as described in connection with the method and the device.

These and other aspects of the invention will be apparent from and elucidated with reference to the embodiment(s) described hereinafter.

BRIEF DESCRIPTION OF THE DRAWINGS

The photoablation device and the method according to the invention are described in greater detail hereinbelow by way of an example embodiment and with reference to the attached drawings, in which.

DETAILED DESCRIPTION

In the following description, certain terms are used for reasons of convenience and are not to be interpreted as limiting. The terms "right", "left", "up" and "down" refer to directions in the figures. The terminology comprises the explicitly mentioned terms as well as their derivations and terms with a similar meaning.

Figure 1:
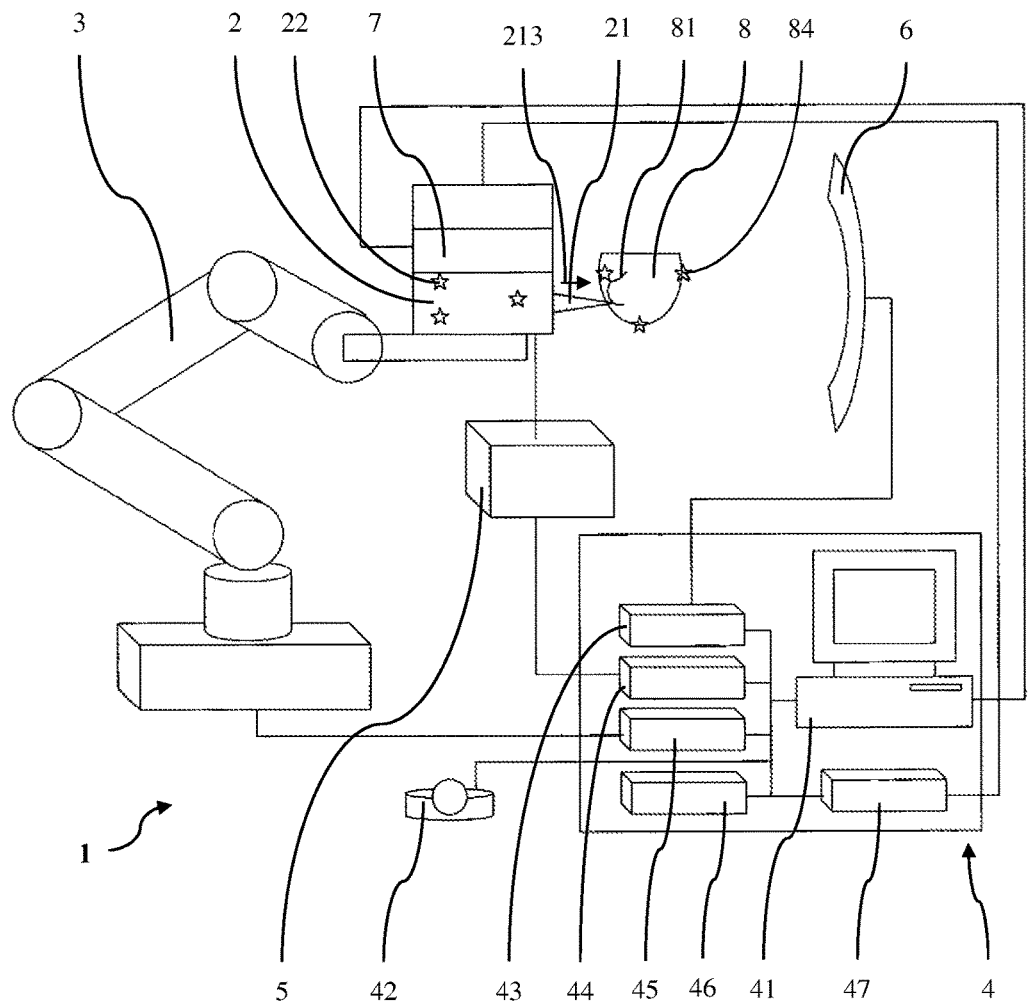
FIG. 1 shows an embodiment of a photoablation device according to the invention.

FIG. 1 shows an embodiment of a photoablation device 1 according to the invention for depth controlled photoablation of a target bone tissue 8. The photoablation device 1 includes a robot arm 3 as positioning device, an evacuation supply system 5, an auto-tracker 6 as position detector, a laser source 2, a microphone 7 as acoustic sensor, and a controller unit 4 having a computer 41.

The laser source 2 is fixedly mounted to a platform provided at a free end of the robot arm 3. It is arranged to propagate a focused laser beam 21 in a direction of propagation 213 which, in FIG. 1, is from left to right. The laser source 2 is connected to a current adjuster 47 of the controller unit 4 which allows the energy intensity of the laser beam 21 to be adjusted by adjusting the current provided to the laser source 2.

The bone tissue 8 is positioned to be reached and targeted by the laser beam 21 of the laser source 2. The robot arm 3 has several degrees of freedom such that the laser source 2 can be moved by the robot arm 3 in order to be accurately positioned and oriented to propagate the laser beam 21 to the bone tissue 8. For controlling the robot arm 3, and particularly its movements, the robot arm 3 is connected to a robot interface 45 of the controller unit 4 such that the computer 41 can control and adjust the position and orientation of the laser source 2.

The auto-tracker 6 is arranged to detect and track the position of the laser source 2 in relation to the bone tissue 8. For allowing three-dimensional detection of the position and orientation, the laser source 2 is provided with at least three markers 22 and the bone tissue 8 is provided with at least three markers 84. The auto-tracker 6 is connected to an auto-tracker interface 43 of the controller unit 4 such that detected positions of the laser source 2 and the bone tissue 8 or particularly their markers 22, 84, respectively, can be gathered and evaluated by the computer 41.

On the bone tissue 8, an osteotomic line 81 is defined via the controller unit 4. In order to cut the bone tissue 8 along the osteotomic line 81, the laser source 2 is moved in relation to the bone tissue 8 such that the laser beam 21 is appropriately propagated. The osteotomic line 81 can be defined in the controller unit 4 by a dataset specifying a linear array of spots. The dataset can include the position of the spots where holes are to be perforated in the bone tissue 8, as well as striking angles of the laser beam 21 with respect to a surface of the bone tissue 8. In particular, the position of each spot can be defined by a set of space coordinates X, Y, and Z, and the striking angle on each spot can be defined by a pair of angles $\theta$ and $\Omega$. Thus, the dataset can include XYZ-$\theta\Omega$ information for each spot, together forming the osteotomic line 81.

The microphone 7 is fixedly located with regard to the laser source 2. It is arranged to sense an acoustic wave generated by the laser beam 21 hitting the bone tissue 8. The microphone 7 is connected to the computer 41 of the controller unit, wherein a signal corresponding to the sensed acoustic wave is transmitted from the microphone 7 to the computer 41. Considering varying frequency spectra of the acoustic waves caused by photoablation in general, and caused by photoablation of different tissue materials, the computer 41 can evaluate the signal transmitted by the microphone 7. Thereby, it can be detected, on the one hand, if photoablation is performed or not and, on the other hand, if and when the target material or properties thereof change.

The controller unit 4 further has a joystick 42 connected to the computer 41 via an osteotomy design interface 46. By using the joystick 41, a practitioner is allowed to design the osteotomic line 81 on the bone tissue 8, wherein the bone tissue 8 can be visually modelled or displayed by any suitable method and means. The evacuation supply system 5 is arranged to evacuate debris resulting from the photoablation of the bone tissue 8, and to supply a medium for keeping the bone tissue 8 clean, particularly near the osteotomic line 81. For this purpose, the evacuation supply system 5 can be equipped with an aspirating pump and/or a water jet. The evacuation supply system 5 is connected to an evacuation supply interface 44 such that the computer 41 can monitor control appropriate supply and evacuation.

The following applies to the rest of this description. If, in order to clarify the drawings, a figure contains reference signs which are not explained in the directly associated part of the description, then it is referred to previous description sections.

Figure 2:
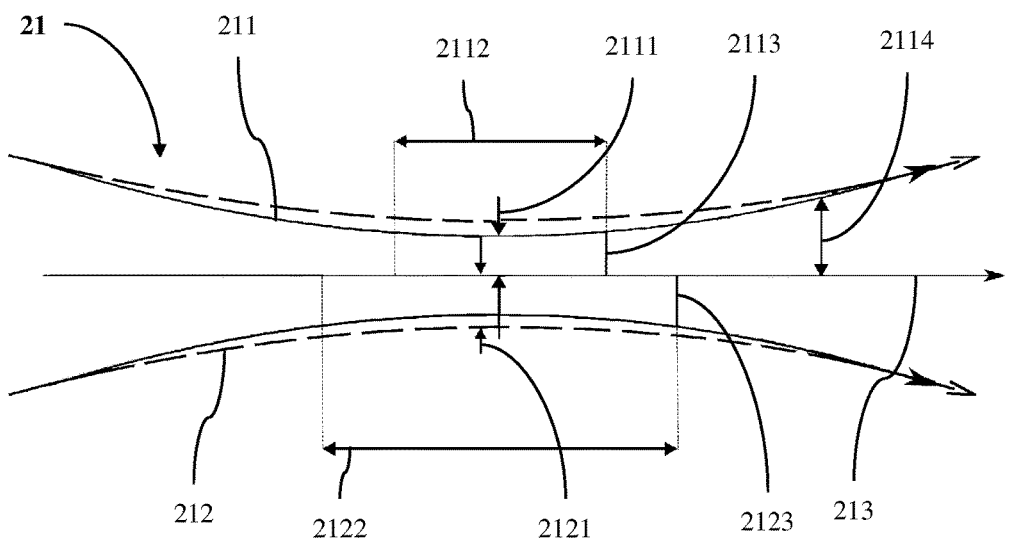
FIG. 2 shows a focused laser beam with a photoablation zone defined in accordance with the invention.

In FIG. 2, the focused laser beam 21 provided by the laser source 2 in the direction of propagation 213 and its tailoring or application in accordance with the invention is shown in greater detail. Generally, the shape of the laser beam 21 is known a priori to be similar as all focused laser beams and looks essentially like an ideal Gaussian laser beam 211 with $M^2=1$ or a non-ideal laser beam 212 with $M^2>1$. The ideal Gaussian laser beam 211 has a waist 2111 of smallest beam radius at which the photon-flux or photon density, which corresponds to the energy density, is highest. Starting from the waist 2111, the beam radius increases in and against the direction of propagation 213, as exemplified by beam radius 2114. Correspondingly, the photon or energy density decreases from the waist 2111 in and against the direction of propagation 213.

In accordance with the invention, a photoablation zone 2112 of the ideal Gaussian laser beam 211 is defined. The photoablation zone 2112 corresponds to a Raleigh zone of the ideal Gaussian laser beam 211 at the end of which its photon and energy intensity drops to half compared to respective intensity at the waist 2111. Outside the Raleigh zone, the so called far-field of the ideal Gaussian laser beam 211 is located. The distal end of the photoablation zone 2112 or the end in the direction of propagation 213 of the photoablation zone 2112 forms a cutting face 2113 of the ideal Gaussian laser beam 211.

Correspondingly, the non-ideal laser beam 212 has a waist 2121 of smallest beam radius which is bigger than, and offset compared to the waist 2111 of, the ideal Gaussian laser beam 211. Starting from the waist 2121 of the non-ideal laser beam 212, the photon or energy density decreases from the waist 2121 in and against the direction of propagation 213. A photoablation zone 2122 of the non-ideal laser beam 211 is defined corresponding to a Raleigh zone. At the end of the Raleigh zone of the non-ideal laser beam 212, the photon and energy intensity drops to half compared to respective intensity at the waist 2121. The distal end of the photoablation zone 2122 or the end in the direction of propagation 213 of the photoablation zone 2122 forms a cutting face 2123 of the non-ideal laser beam 212.

Figure 3:
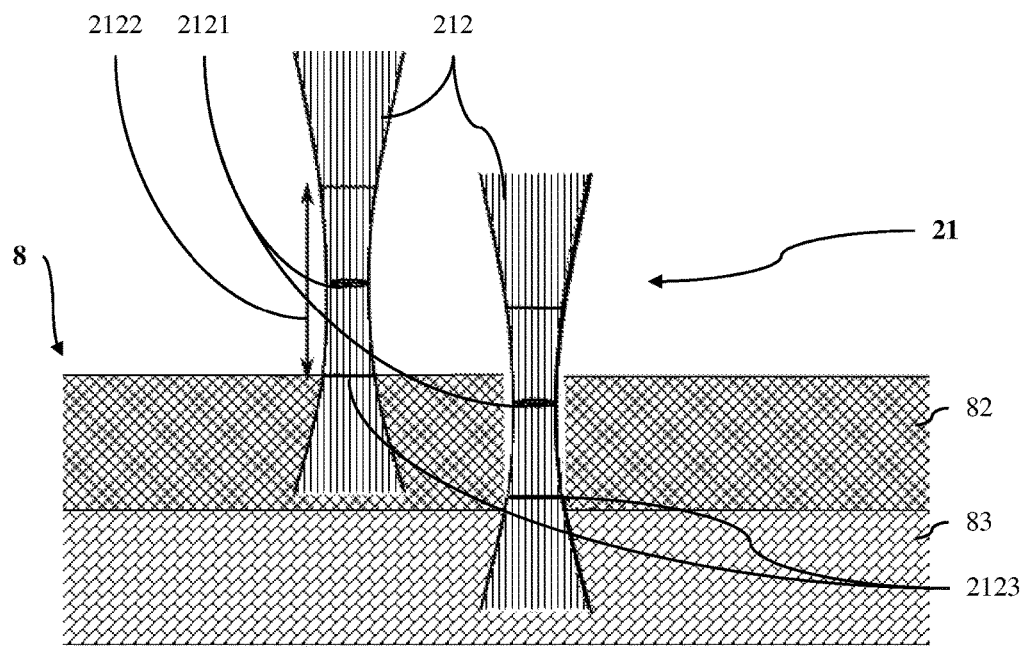
FIG. 3 shows the focused laser beam of FIG. 2 applied to a bone tissue.

FIG. 3 shows the non-ideal laser beam 212 in two different situations, with regard to the bone tissue 8 which has an upper cortical bone portion 82 and a lower spongious bone portion 83. The cortical bone portion 82 and the spongious bone portion 83 have different photoablation properties.

As can be seen in the left-hand situation of FIG. 3, the laser source 2 is positioned and oriented by the controller unit 4 and the robot arm 3, such that the cutting face 2123 of the non-ideal laser beam 212 is arranged at a top surface of the bone tissue 8. Initially, the current adjuster 47 of the controller unit 4 adjusts the current provided to the laser source 21, on a level such that the beam intensity is too low to initiate photoablation of the bone tissue 8 at the cutting face 2123. In this status, the microphone 7 provides a signal, which is evaluated by the computer 41 of the controller unit 4, to be not induced by an acoustic wave for bone photoablation. Then, by increasing the current provided to the laser source 2, the intensity at the cutting face 2123 is increased until the computer 41 of the controller unit 4 evaluates that the respective signal provided by the microphone 7 is indicative for start of photoablation of the bone tissue 8. The current adjuster 47 of the controller unit 4 then holds the current provided to the laser source 21 at this level and the laser source 2 is calibrated. Like this, the laser beam intensity is selected such that the photon-flux only exceeds the threshold required for ablating the bone tissue inside photoablation zone 2122 of the non-ideal laser beam 212. As the robot arm 3 accurately controls the positioning and orientating of the laser beam 21 relative to the bone tissue 8, the cutting depth can thus be precisely controlled by moving the laser source 2 towards the bone tissue 8 as can be seen on the right-hand side of FIG. 3.

Thus, also considering that the bone thickness is usually known, the robot arm 3 can set the focal point of the optic such that the laser energy or density at the desired cutting depth just barely exceeds the required threshold for photoablation bone tissue 8, thus allowing efficient control over the ablation depth. As the photon-flux or laser beam intensity in the far field is below the required threshold, no ablation can happen. Thus, the cutting depth is limited and controlled by a comparably simple physical principle.

While photoablating the bone tissue 8, the microphone continuously provides the acoustic signal and the computer 41 of the controller unit 4 continuously monitors a frequency spectrum of the acoustically sensed wave corresponding to the acoustic signal. Once it is detected that frequency spectrum changes due to changing properties of the tissue being ablated, the laser beam intensity is decreased and photoablation is stopped. The laser beam 21 can then be recalibrated as described above. For example, once the non-ideal laser beam 212 reaches the transition from the cortical bone portion 82 to the spongious bone portion 83, the acoustic signal provided by the microphone 7 changes. The computer 41 of the controller unit 4 evaluates that the frequency spectrum of a wave corresponding to this changed signal represents changed photoablating properties of the bone tissue 8, and the controller unit 4 decreases the current provided to the laser source 2 to a level at which no photoablation occurs. Now, similar to the initial calibration, the laser source is recalibrated in accordance with the properties of the spongious bone portion 83.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present disclosure covers further embodiments with any combination of features from different embodiments described above and below.

The invention also covers all further features shown in the figures individually, although they may not have been described in the above or following description. Also, single alternatives of the embodiments described in the figures and the description and single alternatives of features thereof can be disclaimed from the subject matter of the invention or from disclosed subject matter. The disclosure includes subject matter including the features defined in the claims or the exemplary embodiments as well as subject matter including these features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. A computer program may be stored/distributed on a suitable medium, such as an optical storage medium or a solid-state medium supplied together with or as part of other hardware, but may also be distributed in other forms, such as via the Internet or other wired or wireless telecommunication systems. In particular, e.g., a computer program can be a computer program product stored on a computer readable medium which computer program product can have computer executable program code adapted to be executed to implement a specific method such as the method according to the invention. Any reference signs in the claims should not be construed as limiting the scope.

The invention claimed is:

1. A photoablation device for depth controlled photoablation cutting of human or animal tissue, the photoablation device comprising:
    a laser source being arranged to propagate a focused laser beam with a beam waist, wherein a radius of the laser beam increases from the beam waist in a direction of propagation of the laser beam;
    an adjusting structure being arranged to adjust an intensity of the laser beam, wherein the intensity is energy per time per area;
    a position detector to detect a position of the laser source in relation to the tissue;
    a positioning device being arranged to move the laser source in relation to the tissue; and
    a controller unit being arranged to:
        define a photoablation zone of the laser beam, wherein the photoablation zone ends in a cutting face which is located offset from the beam waist in the direction of propagation of the laser beam;
        position the laser source using the positioning device so that the cutting face of the photoablation zone is at a top surface of the tissue, wherein the intensity of the laser beam is below a photoablation threshold to cut the tissue by the cutting face;
        adjust the intensity of the laser beam at the cutting face of the photoablation zone using the adjusting structure so that the intensity as adjusted exceeds the photoablation threshold to cut the top surface of the tissue; and
        control a depth of photoablation cutting by the cutting face through the top surface into the tissue by moving the laser source toward the tissue using the positioning device, wherein the position of the laser source detected by the position detector is evaluated.

2. The photoablation device according to claim 1, wherein the adjusting structure comprises at least one of a current adjuster and a pulse adjuster, the current adjuster to adjust at least one of a current and a voltage provided to the laser source propagating the laser beam, the pulse adjuster to adjust a length of a pulse of the laser beam.

3. The photoablation device according to claim 1, further comprising an acoustic sensor being arranged to sense an acoustic wave generated by the laser beam hitting the tissue and to provide a corresponding signal.

4. The photoablation device according to claim 3, wherein the controller unit is arranged to evaluate the signal provided by the acoustic sensor in order to detect photoablation cutting of the tissue.

5. The photoablation device according to claim 4, wherein the controller unit is arranged to continuously increase intensity of the laser beam until photoablation cutting of the tissue is detected by evaluating the signal provided by the acoustic sensor.

6. The photoablation device according to claim 3, wherein the controller unit is arranged to monitor a frequency spectrum of the acoustic wave by evaluating the signal provided by the acoustic sensor.

7. The photoablation device according to claim 3, wherein the acoustic sensor is at least one of a microphone, a piezoelectric pressure transducer, or a laser microphone.

8. The photoablation device according to claim 1, wherein the controller unit is further arranged to adjust the laser beam such that the intensity is below the threshold to cut the tissue by the cutting face of the photoablation zone.

9. The photoablation device according to claim 1, wherein the controller unit is further arranged to continuously increase the intensity of the laser beam at the cutting face of the photoablation zone until the intensity exceeds the threshold to cut the top surface of the tissue.

10. A method of depth controlled photoablation cutting of human or animal tissue, the method comprising:

providing a focused laser beam with a beam waist, wherein a radius of the laser beam increases from the beam waist in a direction of propagation of the laser beam;

defining a photoablation zone of the laser beam, wherein the photoablation zone ends in a cutting face which is located offset from the beam waist in the direction of propagation of the laser beam;

positioning the laser beam so that the cutting face of the photoablation zone is at a top surface of the tissue, wherein an intensity of the laser beam is below a photoablation threshold to cut the tissue by the cutting face of the photoablation zone, wherein the intensity is energy per time per area;

adjusting the intensity of the laser beam at the cutting face of the photoablation zone so that the intensity as adjusted exceeds the photoablation threshold to cut the top surface of the tissue; and controlling a depth of photoablation cutting by the cutting face through the top surface into the tissue by moving the laser beam toward the tissue.

11. The method according to claim 10, wherein the photoablation zone of the laser beam corresponds to a Raleigh zone of the laser beam.

12. The method according to claim 10, wherein the intensity of the laser beam is adjusted by adjusting one or more of: at least one of a current and a voltage provided to a laser source propagating the laser beam; and a length of a pulse of the laser beam.

13. The method according to claim 10, further comprising:

continuously sensing if the tissue is cut by photoablation; and stopping the adjusting of the intensity of the laser beam when it is sensed that the photoablation cutting of the top surface of the tissue starts.

14. The method according to claim 13, wherein the photoablation cutting of the tissue is acoustically sensed by monitoring a frequency spectrum of an acoustically sensed wave.

15. The method according to claim 10, wherein the photoablation of the tissue is optically sensed by applying optical coherence tomography.

16. The method according to claim 10, further comprising:

setting the intensity of the laser beam such that the intensity at the cutting face of the photoablation zone is below a threshold to cut the top surface of the tissue; and continuously increasing intensity of the laser beam until the intensity at the cutting face of the photoablation zone exceeds the threshold to cut the top surface of the tissue.

17. The method according to claim 10, further comprising:

determining properties of the tissue prior to adjusting the intensity of the laser beam; and considering the properties when photoablation cutting the tissue.

18. The method according to claim 10, further comprising adjusting the laser beam such that the intensity is below the threshold to cut the top surface of the tissue by the cutting face of the photoablation zone.

19. The method according to claim 10, further comprising continuously increasing the intensity of the laser beam at the cutting face of the photoablation zone until the intensity exceeds the threshold to cut the top surface of the tissue.

* * * * *